(12) United States Patent
Boyd et al.

US008741266B2

(10) Patent No.: US 8,741,266 B2
(45) Date of Patent: Jun. 3, 2014

(54) CLEANING AND/OR POLISHING COMPOSITIONS AND METHODS OF USE THEREOF

(75) Inventors: Thomas J. Boyd, Metuchen, NJ (US); Thomas S. Campbell, Plainsboro, NJ (US); James G. Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 32 days.

(21) Appl. No.: 11/613,718

(22) Filed: Dec. 20, 2006

(65) Prior Publication Data

US 2007/0140985 A1 Jun. 21, 2007

Related U.S. Application Data

(60) Provisional application No. 60/752,453, filed on Dec. 21, 2005.

(51) Int. Cl.
*A61K 8/02* (2006.01)
*A61K 8/25* (2006.01)
*A61Q 11/00* (2006.01)

(52) U.S. Cl.
USPC .............................. 424/49; 424/401; 424/489

(58) Field of Classification Search
USPC .......................................................... 424/48
See application file for complete search history.

(56) References Cited

U.S. PATENT DOCUMENTS

| | | | |
|---|---|---|---|
| 3,965,026 A | 6/1976 | Lancz | |
| 4,187,288 A | 2/1980 | Cordon et al. | |
| 4,235,874 A | 11/1980 | Norfleet | |
| 4,713,243 A | 12/1987 | Schiraldi et al. | |
| 4,784,788 A | 11/1988 | Lancz | |
| 4,855,067 A | 8/1989 | Jakubicki | |
| 4,869,842 A | 9/1989 | Denis et al. | |
| 4,894,220 A | 1/1990 | Nabi et al. | |
| 5,294,364 A | 3/1994 | Thomas et al. | |
| 5,480,633 A | 1/1996 | Simion et al. | |
| 5,589,160 A | 12/1996 | Rice | |
| 5,833,954 A | 11/1998 | Chow et al. | |
| 5,933,786 A | 8/1999 | Sarpola et al. | |
| 5,939,051 A | 8/1999 | Santalucia et al. | |
| 5,993,786 A | 11/1999 | Chow et al. | |
| 6,290,933 B1 | 9/2001 | Durga et al. | |
| 6,294,155 B1 | 9/2001 | Thomas et al. | |
| 6,294,509 B1 | 9/2001 | Meiwa et al. | |
| 6,379,654 B1 | 4/2002 | Gebreselassie et al. | |
| 6,419,903 B1 | 7/2002 | Xu et al. | |
| 6,419,906 B1 | 7/2002 | Xu et al. | |
| 6,514,483 B2 | 2/2003 | Xu et al. | |
| 6,585,960 B2 * | 7/2003 | Thomas et al. | 424/49 |
| 6,669,929 B1 | 12/2003 | Boyd et al. | |
| 6,669,930 B1 | 12/2003 | Hoic et al. | |
| 6,670,318 B2 | 12/2003 | Hokkirigawa et al. | |
| 6,770,264 B2 | 8/2004 | Stier et al. | |
| 6,770,266 B2 | 8/2004 | Santarpia et al. | |
| 6,946,010 B2 | 9/2005 | Huang | |
| 6,948,873 B2 | 9/2005 | Policicchio et al. | |
| 2004/0042976 A1 | 3/2004 | Silber et al. | |
| 2004/0062724 A1 | 4/2004 | Moro et al. | |
| 2004/0126332 A1 | 7/2004 | Boyd et al. | |
| 2004/0136924 A1 | 7/2004 | Boyd et al. | |
| 2005/0042976 A1 | 2/2005 | Ronay | |

FOREIGN PATENT DOCUMENTS

| | | |
|---|---|---|
| GB | 1 534 680 A | 12/1978 |
| JP | 2006-069983 A | 3/2006 |
| RU | 2005107309 | 8/2005 |
| RU | 2307644 | 10/2007 |
| WO | WO 99/43291 A | 9/1999 |
| WO | WO 2004/060335 A | 7/2004 |
| WO | WO 2005/058265 A | 6/2005 |

OTHER PUBLICATIONS

Grace Davison Products, 1999, "Sylodent® Syloblanc® Dentifrice Silica Grades", www.gracedavison.com/products/fcph/sylodent/grade.htm.
Grace Davison Products, 1999, "Sylodent® XWA® Abrasive Silicas Deliver Performance and Value", www.gracedavison.com/products/fcph/sylodent/xwagrd.htm.
Grace Davison, 2005, "HC 800 New High-Cleaning Silica for Dentifrice Applications", Product Information & Technical Info.
Huber Engineered Materials, 2004, "Working with the Essential Elements", pp. 1-14.
Li Gang, 2003, "Physiochemical Property and Type of Abrasive Agents in Toothpaste—Effect of Toothpaste Abrasives on Tooth Wearing and Tooth Cleaning", Chinese Journal of Conservative Dentistry, 13(8):465-468.
PCT/US06/062403—ISR and Written Opinion mailed Jul. 10, 2007.
Ren Yuguang et al., 1991,"Development of Flexible, Moisture-Proof Dental Finishing Disks and Finishing Strips", Journal of First Military Medical University, 11(3):202-206.

\* cited by examiner

*Primary Examiner* — Frederick Krass
*Assistant Examiner* — Isaac Shomer
(74) *Attorney, Agent, or Firm* — Howard C. Lee

(57) ABSTRACT

Compositions for cleaning and/or polishing are provided. The compositions comprise a first abrasive, a film comprising a second abrasive, and a carrier. The carrier can be in the form of an oral care composition, a personal care composition, a household care composition, and the like. The present invention also provides methods of cleaning and/or polishing a target surface.

16 Claims, No Drawings

CLEANING AND/OR POLISHING COMPOSITIONS AND METHODS OF USE THEREOF

CROSS REFERENCE TO RELATED APPLICATION

The present application claims benefit of U.S. Provisional Application No. 60/752,453 filed Dec. 21, 2005, which is hereby incorporated by reference in its entirety.

BACKGROUND OF THE INVENTION

Abrasives are often used to clean and/or polish hard surfaces, such as teeth, household fixtures and goods, and the like. Further, such abrasives can also be used in conjunction with personal care compositions, for example as exfoliation products for skin and nails. Generally, the particle size, crystallinity, hardness, and structure, as well as other factors determine whether certain abrasives are more suitable for cleaning or polishing of a surface. The selection of abrasives for any purpose likewise accounts for the surface properties and degree of accompanying mechanical force. Cleaning abrasives are typically used to debride debris, impurities, and stains from a surface. Polishing abrasives create a smooth, glossy appearance on the target surface and can provide further stain removal.

To maximize the effectiveness of a composition that polishes, and preferably also cleans, it is desirable to have increasingly finer or smaller particles contact a surface during processing to provide polishing, also referred to as lapping. Maximizing contact of the particles with the surface provides more efficacious cleaning and/or polishing, particularly when the sequence and duration of contact of different abrasives can be controlled. Further, controlling the physical orientation of polishing particles with respect to the surface is desirable to enhance efficacy of the abrasives. However, there are significant challenges to using both cleaning and polishing abrasives in a single product to achieve the desired effect. Compatibilizing different abrasives in a single carrier can pose difficulties. Additionally, staging release of different species of abrasives, particularly when they are combined in a single product, poses a challenge. Thus, compositions and methods that improve the cleaning and/or polishing of a target surface are desirable.

BRIEF SUMMARY OF THE INVENTION

In various embodiments, an oral composition is provided that comprises a first abrasive, a film comprising a second abrasive, and a carrier.

In certain embodiments, the present invention provides a method of cleaning or polishing a target surface comprising:
contacting the surface with a composition comprising a first abrasive, a film comprising a second abrasive, and a carrier;
disintegrating at least a portion of the film to expose the second abrasive; and
contacting the surface with the second abrasive.

In certain embodiments, the present invention is directed to a method of cleaning or polishing a target surface with a controlled release composition comprising a first abrasive and a second abrasive is provided. The method comprises:
contacting the first abrasive with the surface; and
subsequently contacting the second abrasive with the surface In certain embodiments, the present invention is directed to a method of cleaning or polishing an oral surface comprising:
introducing an oral composition into an oral cavity that comprises a film comprising a polishing abrasive into an oral cavity; and
contacting the film with an oral surface and saliva, wherein during the contacting the film disintegrates into a plurality of successively smaller film fragments, and wherein the contacting of the film with the oral surface polishes the oral surface.

In certain embodiments, the present invention is directed to a composition for cleaning and/or polishing a target surface comprising:
a carrier comprising a cleaning abrasive and a polishing abrasive, wherein the polishing abrasive is activated for polishing subsequent to exposure to the surface or a solvent.

DETAILED DESCRIPTION OF THE INVENTION

Throughout the present disclosure, all references cited are hereby incorporated by reference in their entireties. In the event of a conflict between a definition in a reference and one herein, the present disclosure controls.

The present disclosure relates to compositions and methods for cleaning or polishing of target surfaces, including industrial, household, human and animal somatic surfaces, particularly oral, dermal, and keratinous surfaces. The compositions described herein clean and/or polish such surfaces. As used herein, the term "cleaning" generally refers to the removal of contaminants, dirt, impurities, and/or extraneous matter on a target surface. For example, in the context of oral surfaces, where the surface is tooth enamel, the cleaning preferably removes at least some of a film or stain, such as plaque biofilm, pellicle or tartar. For personal care compositions, the cleaning can remove dead cells, sebum, oils, dirt, and other contaminants. In the case of household or industrial surfaces, the cleaning can remove dirt, grime, scale, oil or other contaminants. "Polishing" generally refers to a finishing or refining process that makes a surface smoother and/or glossier. Polishing and cleaning can also provide brightening of the surface where stain removal occurs, for example, whitening of a tooth surface.

The compositions described herein provide, in various embodiments, cleaning and/or polishing of a target surface. Non-limiting examples of target surfaces include oral surfaces, such as tooth enamel; dermal surfaces, such as skin; keratinous surfaces, such as nails and hair; household surfaces, such as hardware, fixtures, tableware, home goods, tiles, floors, walls, appliances, ceramics, metals and the like.

Thus, in certain embodiments, a composition for cleaning or polishing a target surface comprises a carrier comprising a first abrasive and a second abrasive. The composition provides controlled release, or controlled activation, of the second abrasive. The second abrasive is preferably activated upon exposure to the target surface to be treated. The term "activated" refers to a process of making the abrasive available for effectively treating the target surface for its intended effect; for example, making a polishing abrasive available for polishing the target surface. The compositions may be maintained such that the first and the second abrasives are either separately kept or stored in localized regions within the carrier (non-homogenously distributed through the carrier). Thus, in accordance with various embodiments, the second abrasive is stored in a non-activated state, where it is not fully available for its intended purpose. The second abrasive is activated upon exposure to a target surface, optionally in the presence of a solvent, and/or a mechanical force, such that it can then be effectively used for its intended purpose, e.g., polishing.

For example, where the composition comprises a film comprising the second abrasive, it may be activated when at least a portion of the film disintegrates to expose a portion of the second abrasive. As used herein, "disintegrate" means that the film breaks or decomposes into smaller pieces, fragments, or parts, for example. The disintegration may be achieved by chemical disruption, mechanical disruption, or both, simultaneously or serially.

In certain embodiments, the film stays substantially suspended and undisintigrated while in the carrier, but the application of shear force and/or exposure to solvent(s), such as water, disrupts and breaks the film into fine pieces. In some embodiments, an abrasive can be totally contained within the film, or partially exposed on the surface of the film. The term "abrasive" as used herein refers to a particle that abrades a target surface. The term encompasses a plurality of abrasive particles. As the disintegration process proceeds, the activation of the second abrasive contained within the film entails sufficient exposure of the surface of the abrasive (i.e., of a sufficient number of abrasive particles) to achieve the desired effect. For example, in various embodiments, at least about 10% of the total surface area of the plurality of abrasives contained in the film are available for contact with the surface after a short time duration of exposure to the target surface. In various embodiments, the available surface area is greater than about 25%, greater than about 30% or greater than about 50%.

Likewise, in certain embodiments, the second abrasive is encapsulated in a protective coating, and is activated by disintegration of at least a portion of the protective coating. In other embodiments, the individual particles of the polishing abrasive can be agglomerated into clusters, where polymers or adhesives bind individual particles of the abrasive species together. The agglomerated second abrasive is suspended within the carrier, and thus is distributed in localized clusters. When the composition is exposed to a target surface and/or a solvent, optionally with mechanical force applied, the polymer or adhesive binding the clusters disintegrates, thus releasing the individual particles of the second abrasive and activating the second abrasive for its intended purpose. Thus, the individual abrasive particles are released and available for polishing the target surface. Accordingly, in various embodiments, the protective coating, adhesive/binding agent, and/or film comprises a material capable of disintegrating in the presence of a solvent, mechanical force or contact with the target surface.

In certain embodiments, a method of cleaning and/or polishing a target surface comprises contacting the surface with a composition that comprises a first abrasive, a film comprising a second abrasive, and a carrier. As described above, in certain embodiments at least a portion of the film is disintegrated to expose at least a portion of the second abrasive, such that it is activated. The exposed portion of the second abrasive is then contacted with a target surface.

In various embodiments, the contacting of the first abrasive and the contacting of the second abrasive occur concurrently. The contacting of the first abrasive with the target surface occurs for a first time duration and the contacting of the second abrasive with the target surface occurs for a second time duration. In various embodiments, the second time duration initiates after the initiation of the first time duration. In this manner, the second abrasive is activated and exposed for its intended purpose after the contacting of the first abrasive with the target surface. This delayed activation of the second abrasive is believed to improve the efficacy of both the first and second abrasives, by sequentially staging the respective exposure of the first and second abrasives to the target surface.

For example, where the first abrasive is a "cleaning abrasive" (that is, an abrasive whose main purpose is cleaning as described above) and the second abrasive is a "polishing abrasive" (that is, an abrasive whose main purpose is polishing as described above), the subsequent activation or release of polishing abrasive is believed to improve the polishing effects. Effective polishing of a surface typically occurs by contacting a target surface with increasingly smaller particles, which is facilitated when the second time duration initiates after the initiation of the first time duration.

Thus, in various embodiments, a composition is provided that comprises a first abrasive, a second abrasive, and a carrier. As appreciated by one of skill in the art, the amount of the abrasive present in the composition is dependent upon various non-limiting factors, including the characteristics of the individual abrasives, the degree of cleaning and polishing to be performed on the target surface, and the compatibility of the abrasives with the carrier and/or film, for example.

In various embodiments, the first abrasive is present in an amount of about 1% to about 70% by weight of the composition, about 5% to about 50% or about 7% to about 40%. In various embodiments, the second abrasive is present in an amount of about 0.5% to about 20% by weight of the composition, about 1% to about 15% and about 2% to about 10%. In certain embodiments where a film comprises the second abrasive, the second abrasive is present in an amount of about 5% to about 40% by weight of the film, or about 3 to about 25% by weight of the film. In certain embodiments, the film is present in an amount of about 0.01% to about 50% by weight of the composition.

As discussed above, cleaning and polishing abrasives can be classified by various physical parameters. A single abrasive species may perform at least some cleaning and polishing simultaneously. However, particles are generally categorized in the art by the predominant effect they have on the target surface. Typically, "polishing abrasives" are considered to be relatively small particles having high hardness, as where abrasives with relatively large particle sizes and low hardness are considered to be "cleaning abrasives." Further, the behavior the abrasive exhibits as it interacts with the surface may indicate how well it will lap or polish the surface, as a desirable polishing agent usually degrades into progressively smaller fragments as contact with the surface proceeds. The lapping behavior relates to the ease with which an abrasive breaks down to a successively finer particle sizes, and is generally believed to be based on the abrasive particle's crystalline shape, lines of cleavage, and friability, for example.

Thus, an abrasive is generally categorized on a gradient extending from softer and larger-particled cleaning abrasives to harder and smaller-particled polishing abrasives, but in various embodiments will have abrasive qualities on at least some surfaces. In certain embodiments, the first abrasive is a distinct species from the second abrasive, meaning that each abrasive has a different effect on the target surface; for example, categorized in a different category on the abrasiveness gradient. Any number of abrasives can be selected in this manner. Thus, in certain embodiments, the first abrasive may be a relatively low cleaning abrasive and the second abrasive may be a relatively high cleaning abrasive. For example, the first abrasive may be a cleaning abrasive and the second abrasive may be a polishing abrasive. The present compositions optionally comprise a plurality of different abrasive species, and are not solely limited to first and second abrasives.

Thus, in certain embodiments, the first abrasive has a first particle size and the second abrasive has a second particle size. In certain embodiments, the first particle size is greater than the second particle size. In certain embodiments, the first abrasive has a particle size of about 5 μm to about 15 μm. In certain embodiments, the second abrasive has a particle size of about 0.5 μm to about 5 μm.

Other parameters are also useful for categorizing abrasiveness of particles, including for example, hardness. Hardness can be expressed by a number of different tests known to those of skill in the art, including the Einlehner, Knoop, Vickers, and Rockwell hardness tests, and the Mohs scale of hardness. In certain embodiments, the first abrasive is a cleaning abrasive that generally has a hardness of less than or equal to the target surface to be treated, and the second abrasive is a polishing abrasive that generally has a hardness of greater than or equal to the target surface to be treated. In various embodiments, an abrasive has a Mohs hardness of greater than 1. In certain embodiments, such as those where the surface is tooth enamel, cleaning abrasives have a Mohs hardness of about 1 to about 4. The desirable hardness varies based on the hardness of the target surface. Likewise, in various embodiments, polishing abrasives have a Mohs hardness of greater than about 4, or about 4 to about 9.

The structure of a particle also often reflects abrasiveness. A relatively low structure tends to have higher abrasiveness and a relatively high structure abrasive tends to have lower abrasiveness. Particle structure may be indicated by absorption of linseed oil or dibutyl phthalate (DBP) per 100 grams. Oil absorption values can be measured using the ASTM Rub-Out Method D281. In certain embodiments, a first particle has an oil absorption structure of greater than about 90 cm$^3$/100 g, and the second abrasive has an oil absorption structure of less than about 90 cm$^3$/100 g.

In the context of oral care, the efficacy of the abrasive can be expressed based on a cleaning or an abrasion basis for a dentifrice, namely the pellicle cleaning ratio (PCR) or the radioactive dentin abrasion (RDA) respectively. Methods of performing PCR and RDA are described in U.S. Pat. No. 5,939,051 to Santalucia et al. and U.S. Pat. No. 6,290,933 to Durga et al. Ideally, RDA values for an oral composition should be below about 250 to protect tooth enamel/dentin. In various embodiments where the target surface is an oral surface such as a tooth, an oral composition comprises a first abrasive in an exemplary dentifrice such as those described in the methods above, having a PCR of greater than or equal to about 40, or greater than about 50; and a second abrasive having a PCR of greater than or equal to about 80, or greater than or equal to about 90. In other embodiments, the oral composition has a first abrasive having an RDA of greater than or equal to about 75 and a second abrasive having an RDA of less than or equal to about 250, or less than about 200, but greater than about 100.

In various embodiments, an exemplary polishing abrasive has a particle size of about 0.5 μm to about 5 μm, a Mohs hardness of about 4 to about 8, a pellicle cleaning ratio in an exemplary dentifrice of greater than about 80, an RDA of less than about 250, an oil absorption of less than about 90 cm$^3$/100 g, in various embodiments less than about 80 cm$^3$/100 g or less than about 50 cm$^3$/100 g.

Suitable abrasives include without limitation: silica, silicate, silicon, alumina (including calcined aluminum oxide), aluminosilicates, such as bentonite, zeolite, kaolin, and mica, siliceous or diatomaceous earth, pumice, calcium carbonate, cuttlebone, insoluble phosphates, composite resins, such as melamine resin, phenolic resin, and urea-formaldehyde resin, polycarbonate, silicon carbide, boron carbide, microcrystalline wax, microcrystalline cellulose, including combinations of colloidal microcrystalline cellulose and carboxymethylcellulose, commercially available under the trade name AVICEL® from FMC Biopolymer (Philadelphia, Pa., USA) and combinations and derivatives thereof. As used herein, "mica" refers to any of a group of hydrous aluminum silicate minerals with plate morphology and perfect basal (micaceous) cleavage. Mica can be, for example, sheet mica, scrap mica or flake mica, as exemplified by muscovite, biotite or phlogopite type micas.

Insoluble phosphates useful as abrasives include orthophosphates, polymetaphosphates and pyrophosphates. Illustrative examples include dicalcium orthophosphate dihydrate, dicalcium phosphate dihydrate, calcium hydrogen phosphate, calcium pyrophosphate, β-calcium pyrophosphate, tricalcium phosphate, calcium metaphosphate, potassium metaphosphate, and sodium metaphosphate.

In certain embodiments, such as those wherein the composition is suitable for cosmetic or oral use with humans or other animals, any orally or cosmetically acceptable abrasive can be used for an oral care or personal care composition. In the case of the oral care composition, abrasive selection may account for the abrasive type, fineness (particle size), particle size distribution, and amount of abrasive, to ensure that tooth enamel is not excessively abraded in normal use of the composition.

In the preparation of an oral or a personal care composition, useful abrasives may include silica abrasives such as precipitated silicas having a mean particle size of up to about 20 microns, such as ZEODENT®115, marketed by J. M. Huber (Havre de Grace, Md., USA), which has an average particle size of about 8 to about 14 μm with an oil absorption of greater than about 90 cm$^3$/100 g.

In embodiments where the dentifrice is a clear or transparent gel, an abrasive of colloidal silica, such as those sold under the trademark SYLOID® as SYLOID® 72 and SYLOID® 74 or under the trademark SANTOCEL® 100 alkali metal alumina-silicate complexes are particularly useful, since they have refractive indices close to the refractive indices of gelling agent-liquid (including water and/or humectant) systems commonly used in dentifrices. Such embodiments may be desirable when the films have an aesthetic or decorative function in the carrier.

Useful polishing abrasive materials for preparing oral compositions include high cleaning, low structure silica abrasives, such as those marketed under the trade designation SYLODENT® XWA or SYLODENT® 783 by Davison Chemical Division (W. R. Grace & Co., Baltimore, Md., USA). SYLODENT® XWA 650 is a silica hydrogel composed of particles of colloidal silica. Exemplary silica hydrogels may comprise colloidal particles of silica having an average particle size of about 3 μm to about 12 μm, or about 5 μm to about 10 μm in other embodiments; with a pH range of about 4 to about 10, or about 6 to about 9, when measured as a 5% by weight slurry. The particles of the XWA 650 contain about 10% to about 35% by weight water, have a mean particle size of about 5 μm to about 12 μm, an Einlehner hardness of greater than or equal to about 5 to about 20 mg loss per 100,000 revolutions, an oil absorption of less than about 90 cm$^3$/100 g, for example about 40 cm$^3$/100 g to about 90 cm$^3$/100 g, typically about 70 cm$^3$/100 g. The abrasives have a Brunauer, Emmett and Teller (BET) surface area from 100 to 700 m$^2$/g. XWA 650 has a brightness of 96.8 technidyne. Such abrasives are discussed in U.S. Pat. No. 6,290,933 to Durga et al.

Another useful high cleaning silica abrasive useful with the present invention is marketed as SYLODENT® XWA 300 and is a silica hydrogel containing about 10% to about 25% water by weight, where the mean particle size is about 2 μm to about 4 μm. The particles have BET surface are in the range of 150 to 400 $m^2/g$ of silica. The XWA 300 abrasive has an oil absorption of less than 90 $cm^3$/100 g silica; and a pH, in a 5% w/w suspension in boiled ($CO_2$ free) demineralized water, equal to or greater than 8.5. Such abrasives are discussed in U.S. Pat. No. 5,939,051 to Santalucia et al.

Another suitable high cleaning silica abrasive comprises a silica product, where the particles are about 5% to about 35% by weight water, having a mean particle size of about 7 μm to about 11 μm, an Einlehner hardness of from 12 to about 19, an oil absorption value of about 50 $cm^3$/100 g to about 65 $cm^3$/100 g. A BET surface area is about 100 to about 700 $m^2/g$ of silica. The brightness is generally reported to be greater than about 95 technidyne. Such a silica product is commercially available as ZEODENT® 105 from J. M. Huber (Havre de Grace, Md., USA).

Another high cleaning silica abrasive useful herein has a DBP structure of 100 $cm^3$/100 g, an average maximum particle size of about 13 μm, a pH of about 6 to about 8 (in a 5% aqueous suspension) and a BET surface area of 50 $m^2/g$. Such a silica abrasive is commercially available as HC 800 from Grace. Yet another suitable silica abrasive useful as a polishing agent is a substantially monodisperse silica abrasive having an average particle diameter of about 2 μm.

Thus, in certain oral or personal composition embodiments, the first abrasive may be chosen from silica, alumina, calcium carbonate, and dicalcium phosphate. Likewise, in certain embodiments, the composition is safe for oral and/or somatic contact, and the second abrasive can be chosen from silica, silicate, aluminosilicate, alumina, calcium carbonate, calcium hydrogen phosphate, mica, zeolite, kaolin, siliceous or diatomaceous earth, silicon, cuttlebone, pumice, composite resin, polycarbonate, boron carbide, microcrystalline wax, microcrystalline cellulose or derivatives thereof.

Polishing abrasives for household products can be any of those discussed above, but may also include silicon carbide, aluminum oxide and calcium carbonate. Household cleaning solutions typically contain abrasives that may also serve as detergent builders. A non-limiting list of such additional suitable abrasives for household/home care cleaning products includes: polyphosphates, including pyrophosphates, such as tetrasodium or tetrapotassium pyrophosphates, tripolyphosphates, tetrapolyphosphates, alkali metal carbonates and the like. However, selection of such abrasives is known in the art, and typically is highly dependent on the scratch resistance of the household surface/application.

A method of cleaning and/or polishing an oral surface comprises introducing an oral composition into an oral cavity. As discussed above, in certain embodiments, the oral composition comprises a film that comprises a second abrasive, such as a polishing abrasive. The film is then contacted with an oral surface and saliva. The film degrades into a plurality of successively smaller film fragments during the contacting with the oral surface and/or the saliva. While not limiting as to the present invention, it is believed that the successively smaller film fragments that are produced via the disintegration process improve polishing efficacy by exposing the surface to continuously smaller fragments containing the particles. The kinetically delayed release of the polishing particles is believed to improve polishing performance, by increasing local concentration of the polishing abrasive near the oral surface following the treatment with the larger, softer, cleaning abrasive particles, which may occur during the earlier stage of brushing. The contacting of the film having abrasives with the oral surface may augment and improve the cleaning/polishing of the oral surface.

The films of the present invention may have a substantially lamellar structure. A "lamellar" structure has a size in one or two dimensions (e.g., the x- or y-dimensions) that is substantially greater than the thickness of the structure in a third dimension (e.g., the z-direction), and generally including substantially planar, layered, or lamelliform shapes, for example. In certain embodiments, the lamellar structure is substantially planar, having a size in both the x- and y-dimensions that is substantially greater than that in the z-dimension. In other embodiments, the lamellar structure is non-planar.

Expressed in another way, the films may have an aspect ratio of about 5:1 or greater. Generally, an aspect ratio (AR) is defined as AR=L/D where L is the length of the longest dimension and D is the length of its shortest dimension. In certain embodiments, a film comprises a substantially continuous surface that can appear as a substantially flat surface, although in some embodiments the film may be deformed. In such embodiments, the film can have any of a number of shapes, including having a smooth, curved surface. Further, the term "film" encompasses both a single structure as well as a plurality of film fragments. In various embodiments, the film comprises a plurality of fragments independently having a thickness of about 0.1 mils to about 10 mils, about 0.5 mils to 9 mils, or about 1.2 mils to about 3 mils. In certain embodiments, the length of the fragments is at least about 0.2 mm. The film provided in the carrier as fragments can be provided as film flakes or pieces, or cut into a decorative shape, such as a rectangle, a square, a circle, a triangle, a polygon, a star, a diamond, and the like.

Examples of useful films include those described in U.S. Pat. No. 6,669,929 to Boyd et al.; United States Patent Publication Nos. 2004/0126332, 2004/0136924, and 2004/0042976 all to Boyd et al. Useful films may be rigid or plastic, comprising any of a variety of materials, including forming materials, clays, waxes, and mixtures thereof. In some embodiments, a film comprises at least one film-forming material; in certain embodiments, this film-forming material comprises a polymer. Useful polymers include hydrophilic polymers and hydrophobic polymers. In some embodiments, the polymer is soluble in a solvent, for example, water. For example, a water-soluble, breakable polymer that dissolves during application of physical force during use, such as during tooth brushing or scrubbing while cleaning with a brush or pad may be desirable. In some embodiments, the polymer is insoluble but breakable in water by being dispersible, i.e., the polymer breaks down into small fragments, for example, as a result of shearing. In some embodiments, a polymer is insoluble but swellable, so long as at least a portion of the second abrasive is exposed. Where a polymer does not fully break down during use, the polymer can be a water-repellant polymer or an aqueous-stable hydrophilic polymer such as certain types of cellulose, for example paper.

The polymers may be selected and apportioned in the film to provide at least one of the following: (1) a desired stability of the film in the carrier, (2) a desired rate of disintegration of the film during use of the composition, or (3) a desired rate of exposure of the second abrasive during use of the composition. Such polymers may also be suitable as encapsulating materials and/or binding materials for agglomerates.

In certain embodiments, the film is water-soluble. The film thus comprises a polymer chosen from water soluble polymers, water dispersible polymers, and water insoluble polymers. The relative amounts of water-insoluble polymer, water-soluble polymer, and, optionally, water-soluble filler may be selected to expose an amount of second abrasive proportional to how vigorously or how long the composition is used, e.g., by brushing, scrubbing, or other mechanical action during use of the aqueous composition.

In certain embodiments, the polymer is a water-soluble polymer. One example is a cellulose ether polymer, including those chosen from hydroxyalkyl cellulose polymers such as hydroxypropyl methyl cellulose (HPMC) commercially available from the Dow Chemical Company (Midland, Mich., USA) as METHOCEL® products, including, for example, METHOCEL® E5LV, METHOCEL® E50, and METHOCEL® K100, hydroxypropyl cellulose (HPC), hydroxyethyl cellulose (HEC), methyl cellulose (MC), carboxymethyl cellulose (CMC), or mixtures thereof. Other useful polymers include polyvinylpyrrolidone (PVP), which can have a weight average molecular weight of about 100,000 to about 1.5 million, vinyl acetate, polyvinylpyrrolidone-vinyl acetate copolymers such as KOLLIDON® VA64 (available from BASF, 60:40 by weight vinyl pyrrolidone) and PLASDONE® S630 PVP (available from International Specialty Products, Wayne, N.J., USA, 60:40 by weight vinyl pyrrolidone:vinyl acetate), ethylene oxide graft copolymers of PVA such as KOLLICOAT® IR (available from BASF, 75% by weight PVA, 25% by weight polyethylene glycol graft, polyvinyl alcohol (PVA), acrylates and polyacrylic acid, including polyacrylate polymer, cross-linked polyacrylate polymer, cross-linked polyacrylic acid (e.g, CARBOPOL®), methacrylates, maleic poly vinylalkyl ether-maleic acid copolymer (e.g., GANTREZ®), polyalkylene oxides, including polyethylene oxide, i.e. polyethylene glycol, and carboxy vinyl polymer. As appreciated by a skilled artisan, the film may comprise derivatives, copolymers, and further combinations of such polymers, as well.

Useful water-insoluble polymers include polymers soluble in at least one organic solvent. For example, acrylic copolymers (where carboxylic acid functionality has not been neutralized), cross-linked poly(vinyl pyrrolidone), for example KOLLIDON® CL or CL-M available from BASF, poly(vinyl acetate) [PVAc], certain cellulose derivatives such as cellulose acetate, cellulose nitrate, alkyl cellulose such as ethyl cellulose, butyl cellulose, and isopropyl cellulose, cellulose acetate phthalate, shellac, ethylene-vinyl acetate copolymers, vinyl acetate homopolymer, silicone polymer (e.g., dimethylsilicone), polymethyl methacrylate (PMMA), polymers insoluble in organic solvents, such as cellulose, polyethylene, polypropylene, polyesters, polyurethane and nylon, natural or synthetic rubber, and combinations thereof. An example of a suitable, film-forming acrylic copolymer is LUVIMER®30E, a 30% by weight solution in ethanol of a tert-butyl acrylate/ethyl acrylate/methyacrylic acid copolymer commercially available from BASF (Florham Park, N.J., USA). The water-insoluble polymers may be prepared as dispersions (e.g., by emulsion polymerization) and may be stabilized with suitable emulsifiers. One useful PVAc emulsion, for example, is KOLLICOAT® SR 30D, a 30 weight % dispersion of PVAc in water stabilized with 2.7 weight percent PVP and 0.3% sodium lauryl sulfate. An example of an acrylic copolymer dispersion is KOLLICOAT® EMM 30 D, a 30% by weight aqueous dispersion of an ethyl acrylate: methyl methacrylate copolymer (weight ratio of ethyl acrylate to methyl methacrylate approximately 2 to 1) with a reported average molecular weight of about 800,000, available from BASF.

Other useful polymers or water-soluble fillers include, without limitation: natural gums such as sodium alginate, carrageenan, xanthan gum, gum acacia, Arabic gum, guar gum, pullulan, agar, chitin, chitosan, pectin, karaya gum, zein, hordein, gliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g., hydroxypropylated high amylose starch), dextrin, levan, elsinan and gluten; and proteins such as collagen, whey protein isolate, casein, keratin, milk protein, soy protein, and gelatin. The film may further include dispersible or swellable fillers such as modified starch, alginate esters, divalent or multivalent ion salts of alginates.

In embodiments directed to an aqueous composition, the relative amounts of water-soluble polymer and water-insoluble and/or partially water-soluble polymer in the film may be such that the film is storage-stable in an aqueous composition but disintegrates during use of the composition. In various embodiments, the film may include an amount of water-soluble polymer of about 0.1 to about 90%, about 1 to about 80%, about 5 to about 70%, about 9 to about 50% or about 10 to about 40% by weight of the film. In addition to, or instead of, the water-soluble polymer(s), the film may include partially water-insoluble or water-swellable polymers in amounts of about 0.1 to about 50% by weight of the film, or about 1 to about 10% in other embodiments. In various embodiments, a method of stabilizing hydrophilic films in an aqueous carrier environment uses water-soluble and water-insoluble materials in the film that are balanced for stability while stored in the product carrier, but disintegrate upon use to activate the second abrasive contained therein.

In certain embodiments, oils are included in the film (or optionally in the carrier) that may adhere to the target surface. When selected to have a proper refractive index, the oil accentuates the intensity of light reflected from the polished surface, thus enhancing perception of gloss/sheen. Other optional materials can be included in the film, such as, without limitation: surfactants, emulsifiers, plasticizers such as mineral oil, glycerol, and propylene glycol, clays, inert starch particles, cellulose, or other fillers, waxes, texture modifiers such as cold water swellable, physically modified and pregelatinized starches, and colorants.

In certain embodiments, the films can be prepared using conventional extrusion or solvent casting processes. For example, to prepare a film by solvent casting, a film forming polymer is soluble or dissolved in a sufficient amount of a solvent that is compatible with the polymer. Examples of typically suitable solvents include water, alcohols, acetone, ethyl acetate or mixtures thereof. After a solution has been formed, a plasticizer can be added with stirring, and heat can be applied if necessary to aid dissolution, until a clear and homogeneous solution has been formed, followed by the addition of the abrasives and any additional ingredients, such as bulking agents, plasticizers, surface active agents, flavors and/or sweeteners. The solution can be coated onto a suitable carrier substrate material and dried to form a film. In certain embodiments, the substrate has a surface tension that allows the polymer solution to spread evenly across the intended substrate width without soaking in to form an impermissibly strong bond between the two substrates. Examples of suitable carrier substrate materials include glass, stainless steel, PTFE commercially available as TEFLON® (DuPont, Wilmington, Del., USA), polyethylene-impregnated Kraft paper or polyester plastic liners.

Drying of the film can be carried out in a moderate to high-temperature air-bath using a drying oven, drying tunnel, vacuum drier, or any other suitable drying equipment that does not adversely affect the active ingredient(s) or flavor of the film. During drying, the films can undergo preferential stretching or other alignment processes, such as directional air blown along a predetermined axis of the film to align abrasive particles to have a desired alignment within the film. Shaping of the dry film into fragments or shapes in a final form is possible via simple blade cutting, rotary or punch press dies. Optionally, the carrier substrate may have molds formed therein and the slurry may dry in the molds to a pre-determined shape defined by the mold.

In some embodiments, a substantially axial alignment of abrasive particles is created within the film. An axial alignment refers to the alignment of abrasive particles along at least one axis of the film, such that the abrasive/film matrix has an anisotropic orientation. Thus, the second abrasive in the film may have a substantially axial alignment within the film, meaning each of the plurality of individual particles have substantially the same axial orientation in the film. Since many abrasive particles have irregular shapes, the alignment of abrasives within the film can provide a more planar orientation. Thus, a film comprising an aligned abrasive can provide greater surface area exposure as compared with a primarily spherical and/or irregular shaped particle that is dispersed throughout the carrier (in the absence of a film). Therefore, a substantially axial alignment of abrasive in the film may permit even more exposure and greater contact of the abrasive with the oral surface, which improves polishing and/or cleaning performance.

Conventional ingredients that can be used to form the carriers listed above are known to the skilled artisan. The carrier can be a liquid, semi-solid, or solid phase. When the compositions are an oral care or personal care composition, they may be provided in an orally or dermatologically (i.e., cosmetically) acceptable carrier or vehicle. Oral care compositions can be in the form of a dentifrice (including toothpastes, toothpowders, and prophylaxis pastes), confectionaries (including gums, beads and chews), film, paint-on gels, professional polishing formulations or any other form known to one of skill in the art where abrasives are employed. Personal care compositions include: soaps, bath gels, body washes, shampoos, exfoliating scrubs, lotions, nail care products, and the like. Home care compositions include powders, pastes, detergents and cleansers. Selection of specific carrier components is dependent on the desired product form and the intended use of the composition. The carrier may be aqueous, in which case the carrier may comprise about 5% to about 95% water, about 10% to about 80% water or about 20 to about 70% water in various embodiments. In other embodiments, the carrier may be substantially non-aqueous.

In some embodiments, the film further comprises a functional material. As referred to herein, a "functional material" is a material having a desired utility in the composition. In various embodiments, such utilities may include cleansing, protective, therapeutic, cosmetic, aesthetic, decorative, and sensory or combinations thereof. The functional material depends upon the applications for which the compositions are to be used. Examples of functional materials for oral care active materials include, e.g., oral care active ingredients, such as anti-bacterial active agents, anti-tartar agents, anti-caries agents, anti-inflammatory agents, anti-sensitivity agents, enzymes, nutrients, and the like. Examples of personal care functional materials include, e.g., surface active agents, conditioning agents, moisturizers and emollients, enzymes, other proteins, vitamins, and the like. Examples of household care functional materials include, e.g., detergent surface active ingredients, detergent builders, and conditioning agents and the like.

The carriers of the compositions optionally include additional materials, including for example, surface active agents, such as surfactants, emulsifiers, and foam modulators, viscosity modifiers and thickeners, humectants, diluents, fillers, additional pH modifying agents, colorants, preservatives, solvents, and combinations thereof. Any given material may serve multiple purposes within more than one category of materials.

Suitable surface active agents are those that are reasonably stable throughout a wide pH range. These compounds are known in the art, and include non-soap anionic (e.g., sodium lauryl sulfate (SLS), N-myristoyl, and N-palmitoyl sarcosine), nonionic (e.g., Polysorbate 20 (polyoxyethylene 20 sorbitan monolaurate, TWEEN® 20) and Polysorbate 80 (polyoxyethylene 20 sorbitan mono-oleate, TWEEN® 80), Poloxamer 407, available under the trade name PLURONIC® F127 from BASF, Florham Park, N.J., USA), cationic, zwitterionic (e.g., cocamidopropyl betaine and lauramido propyl betaine), and amphoteric organic synthetic detergents.

In embodiments directed to a dentifrice, an exemplary carrier is substantially semi-solid or a solid. Dentifrices typically contain surface active agents, humectants, viscosity modifying agents and/or thickeners, abrasives, solvents, such as water, flavoring and sweetening agents. The oral compositions optionally include other materials, including for example, emollients, moisturizers, mouth feel agents and the like. Examples of suitable carriers for oral compositions are discussed in U.S. Pat. No. 6,669,929 to Boyd et al., U.S. Pat. No. 6,379,654 to Gebreselassie et al., and U.S. Pat. No. 4,894,220 to Nabi et al.

In embodiments where an oral composition is in the form of a confectionary, an exemplary carrier is substantially solid or semi-solid. Confectionary carriers are well known in the art. Preferred confectionaries include chewing gum carriers that generally have a chewing gum base, one or more plasticizing agents, a sweetening agent, and a flavoring agent. Examples of suitable confectionary carriers are found in U.S. Pat. Nos. 5,833,954 and 5,933,786 both to Chow et al. and U.S. Pat. No. 6,770,264 to Stier et al., which are incorporated herein by reference in their entireties.

In certain embodiments where the oral composition is in the form of an orally consumable film, a film containing a second abrasive is dispersed in a film carrier containing a first abrasive. Preferred film carriers include dissolvable films or films having a removable backing, as are known to those of skill in the art. Examples of suitable films can be found in U.S. Pat. No. 4,713,243 to Schiraldi et al., U.S. Pat. Nos. 6,419,903, 6,419,906, and 6,514,483 all to Xu et al., and United States Patent Publication No. 2004/0062724 to Moro et al. The film carrier can be designed to have a dissolution rate corresponding to a pre-determined treatment duration based on the selected polymers. The dissolution rate of the film carrier may be designed to disintegrate or dissolve at a faster rate than the film comprising the second abrasive, thus permitting controlled release of the first abrasive in the carrier film and of the film comprising the second abrasive. The films may be formed of the same film forming materials described above in the context of the film comprising the second abrasive.

In various embodiments, the film may also comprise hydrophobic film forming polymers, either mixed with a hydrophilic film forming polymer to alter dissolution rates of the film composition, as previously described, or as a removable backing layer. Examples of suitable hydrophobic film forming polymers include: polymethyl methacrylate and its copolymers, polyethylene, polypropylene, polyvinyl alcohol, polyesters, ethyl cellulose, propyl cellulose, isopropyl cellulose, butyl cellulose, t-butyl cellulose, cellulose acetate, and derivatives of polyvinyl alcohol such as, for example, polyvinyl acetate, or silicone polymers.

The film carriers may include the additional ingredients described previously in the context of films, including surfactants, emulsifiers, plasticizers, fillers, waxes, texture modifiers, flavoring and/or sweetening agents, and/or colorants.

The carrier films may be made by any conventional film-forming process, such as extrusion or solution casting. In certain embodiments, the films comprising the second abrasive are mixed into the film after solution casting or prior to extrusion. The carrier film thickness may be greater than the film comprising the second abrasive, such that the film fragments are contained within and distributed throughout the film. For example, the thickness may be about 0.5 mils to about 20 mils, with a wider range of thicknesses feasible.

In certain embodiments, the compositions are in the form of a paint-on oral or nail composition where the carrier is non-aqueous. The paint-on carrier is a flowable viscous non-aqueous liquid suspension that is applied to a surface, such as, teeth or nails, by manual application with a soft applicator. In various embodiments, the paint-on oral composition comprises an adhesion enhancing film forming polymer agent that is liquid and hydrophilic, such as polyalkylene glycol polymers, e.g., nonionic polymers of ethylene oxide, or nonionic block copolymer of ethylene oxide and propylene oxide (for example, Poloxamer copolymers). The paint-on carrier also optionally comprises solvents, plasticizers, bulking, filler, or viscosity modifying agents. Suitable paint-on carriers are discussed in U.S. Pat. No. 6,770,266 to Santarpia et al. and U.S. Pat. No. 6,669,930 to Hoic et al.

Personal care product carriers can be in a wide variety of forms, as previously discussed. For example, the carriers can be emulsions, including, e.g., oil-in-water, water-in-oil, water-in-oil-in-water, and oil-in-water-in-silicone emulsions. These can cover a broad range of viscosities, e.g, about 100 cps to about 200,000 cps. Other suitable carriers include anhydrous liquid solvents such as oils (e.g., vegetable and mineral oils), alcohols (e.g., ethanol, isopropanol) and silicones (e.g., dimethicone, cyclomethicone); aqueous-based single phase liquid solvents (e.g., hydro-alcoholic solvent systems): and thickened versions of these anhydrous and aqueous-based single phase solvents (e.g., where the viscosity of the solvent has been increased to form a solid or semisolid by the addition of appropriate gums, resins, waxes, polymers, salts, and the like. As discussed above, personal care composition carriers may comprise emollients, moisturizers, or conditioning agents, which may also form part of the solvent of the carrier. Soaps, gels, body washes and the like may contain surface active agent detergent(s). Examples of such carriers are discussed in U.S. Pat. No. 5,480,633 to Simon et al.

Home care or household cleaning compositions carriers may comprise a surface active detergent, a detergent builder, such as sulfates (e.g., sodium sulfate), phosphates (e.g., trisodium phosphate, disodium phosphate), complex phosphates (e.g., tetrasodium pyrophosphate, sodium tripolyphosphate, sodium tetraphosphate, sodium hexametaphosphate), silicates (e.g., sodium silicate, colloidal silicates), carbonates (e.g., sodium carbonate, sodium bicarbonate), bleaching compounds (e.g., sodium hypochlorite, sodium perborate, sodium percarbonate), and optional activators, pH buffering agents, enzymes, conditioning agents, diluents, and the like. Exemplary cleansers are described in U.S. Pat. No. 6,670,318 to Hokkirigawa et al., U.S. Pat. No. 5,294,364 to Thomas et al., U.S. Pat. No. 4,869,842 to Denis et al., U.S. Pat. No. 3,965,026 to Lancz, each of which are incorporated herein by reference in their entireties.

The present invention is further illustrated through the following non-limiting examples.

EXAMPLE 1

A film comprising a high cleaning abrasive is prepared using the ingredients listed in Table 1 below.

TABLE 1

| INGREDIENTS | % Composition By Weight |
|---|---|
| Water | 50-95 |
| METHYLCELLULOSE ® E5 | 5-20 |
| TIMERON ® MP-149 | 0.05-5 |
| Flavor Oil | 1-10 |
| High Cleaning Silica (XWA 650) | 1-10 |
| Canola Oil | 0.05-5 |
| TWEEN ® 80 | 0.01-5 |
| Propylene Glycol | 0.01-5 |
| % Solids | 5-60 |

A film is cast from a water solution, where the amount of solids can vary in the range of about 5% to about 60%. In Table 1, the amount of solids is about 20% to about 35%. Specifically in the example in Table 1, the film is cast from a slurry containing about 70 to about 75% water. The film is wet cast onto a removable polyethylene-coated paper web, and dried in an oven set at 80° C. for 10 minutes. A film comprising an abrasive is thus obtained and can be further processed and/or added into a carrier.

EXAMPLE 2

A film comprising a polishing abrasive is prepared using the ingredients listed in Table 2 below.

TABLE 2

| INGREDIENTS | % Composition By Weight (Slurry Basis) | % Composition By Weight (Estimated on a Dry Basis) |
|---|---|---|
| Water | 45-90 | 1-15 |
| METHYLCELLULOSE ® E5 | 2-20 | 20-45 |
| METHYLCELLULOSE ® E50 | 1-10 | 1-20 |
| Monodisperse Silica Abrasive (diameter = | 1-15 | 15-40 |
| Propylene Glycol | 1-10 | 1-25 |
| Canola Oil | 1-10 | 1-15 |
| TWEEN ® 80 | 0.01-5 | 1-10 |

EXAMPLE 3

A film made according to Example 2 above is added to an oral composition, i.e., a dentifrice carrier with the ingredients listed in Table 3 below.

TABLE 3

| INGREDIENTS | % Composition By Weight |
|---|---|
| Sodium Carboxymethyl | 1.10-5 |
| Polyethylene Glycol 600 (PEG- | 0.5-10 |
| Sorbitol | 25-75 |
| Sodium Saccharin | 0.01-5 |
| Sodium Fluoride | 0.01-5 |
| Tetrasodium Pyrophosphate | 0.01-5 |
| Dye (1% in water) | 0.01-1 |
| Silica Abrasive | 5-30 |
| Silica Abrasive | 1-10 |

TABLE 3-continued

| INGREDIENTS | % Composition By Weight |
| --- | --- |
| Flavor Oil | 0.05-5 |
| Sodium Lauryl Sulfate | 0.05-5 |
| Cocamidopropyl Betaine | 0.01-5 |
| Polishing Film From Example 2 | 0.01-5 |
| Water | Q.S. |

The dentifrice formulation in Table 3 is prepared by dispersing water soluble salts and compounds, sodium saccharin, sodium fluoride, and tetrasodium pyrophosphate, in a conventional mixer under agitation. The humectant(s) e.g., sorbitol, are dispersed in water in a conventional mixer under agitation. The organic thickeners, such as sodium carboxy methylcellulose, are added. The mixture is agitated until a homogeneous gel phase is formed. Into the gel phase is added FD&C Blue #1 dye, and any acid and/or base required to adjust the pH to less than about 7.

The mixture is then transferred to a high-speed vacuum mixer, where the cationic compatible inorganic particulate abrasives and/or thickeners, such as ZEODENT® 115 and 165, are added. The mixture is mixed at high speed for 5 to 30 minutes, under vacuum of about 20 to about 50 mm Hg, preferably about 30 mm Hg. The flavor oil is weighed out and then added to the mixture. Last, the surfactants of the stabilizing surfactant system (PEG-12 and cocamidopropyl betaine, i.e., CAP betaine) and the film prepared according to Example 2 are added to the mixture and mixed for an additional 10 minutes. The resultant product is a homogeneous, semi-solid, extrudable paste or gel product.

The invention claimed is:

1. An oral composition comprising:
a first abrasive, wherein the first abrasive is selected from the group consisting of silica, alumina, calcium carbonate, and dicalcium phosphate;
a water soluble film comprising a second abrasive, wherein the second abrasive is chosen from silica, silicon, silicate, aluminosilicate, bentonite, zeolite, kaolin, mica, alumina, calcium carbonate, cuttlebone, orthophosphate, polymetaphosphate, pyrophosphate, calcium hydrogen phosphate, calcium pyrophosphate, tricalcium phosphate, calcium metaphoshate, potassium metaphosphate, sodium metaphosphate, dicalcium orthophosphate, dicalcium, phosphate dihydrate, siliceous or diatomaceous earth, pumice, resin, melamine, phenolic resin, urea-formaldehyde resin, polycarbonate, boron carbide, silicon carbide, microcrystalline wax, microcrystalline cellulose and derivatives thereof; and
a carrier;
wherein the first abrasive is a cleaning abrasive having a Mohs hardness of about 1 to about 4, and the second abrasive is a polishing abrasive having a Mohs hardness of about 4 to about 9, and the second abrasive is present in an amount of 2% to 20% by weight of the composition; and
wherein the first abrasive has a first particle size and the second abrasive has a seconds particle size, wherein the first particle size is greater than the second particle size
wherein the first abrasive is present in an amount of about 1% to about 70% by weight of the composition;
the second abrasive is present in an amount of about 5% to about 40% by it of the film;
wherein the first abrasive has a hardness that is less than or equal to that of a target surface, and the second abrasive has a hardness of greater than or equal to that of the tar ret surface; and
wherein the film comprises a polymer selected from the group consisting of cellulose ethers, acrylates, methacrylates, polyvinyl alcohol, polyalkylene oxides, polyvinylpyrrolidone, copolymers thereof and mixtures thereof.

2. The composition according to claim 1, wherein the film compromising the second abrasive is present in an amount of about 0.01% to about 50% by weight of the composition.

3. The composition according to claim 1, wherein the first abrasive has a particle size of about 5 μm to about 15 μm.

4. The composition according to claim 1, wherein the second abrasive has a particle size of about 0.5 μm to about 5 μm.

5. The composition according to claim 1, wherein the second abrasive comprises a plurality of particles having a substantially axial alignment within the film.

6. The composition according to claim 1, wherein the film comprises a plurality of fragments independently having a thickness of about 0.1 mils to about 10 mils and a length of at least about 0.2 mm.

7. The composition according to claim 1, wherein the carrier comprises one or more ingredients chosen from oral care active ingredients, surface active agents, viscosity modifiers, thickeners, humectants, diluents, pH modifying agents, emollients, moisturizers, mouth feel agents, sweetening agents, flavoring agents, solvent, water, colorants or preservatives.

8. The composition according to claim 1, wherein the second abrasive is present in an amount of about 3% to about 25% by weight of the film.

9. The composition of claim 1, wherein the first abrasive has an oil absorption structure of greater than about 90 $cm^3$/100 g, and the second abrasive has an oil absorption structure of less than about 90 $cm^3$/100 g.

10. The composition of claim 1, wherein the film has a substantially lamellar structure.

11. The composition of claim 1, wherein the film has an aspect ratio of about 5:1 or greater.

12. A method of cleaning or polishing a target surface comprising:
contacting the surface with the composition of claim 1;
disintegrating at least a portion of the film to expose the second abrasive; and
contacting the surface with the second abrasive.

13. The method according to claim 12, wherein the contacting of the surface with the first abrasive cleans the surface; and wherein the contacting of the surface with the second abrasive polishes the surface.

14. The method according to claim 12, wherein the contacting of the first abrasive and the contacting of the second abrasive occur concurrently.

15. The method according to claim 14, wherein the contacting of the first abrasive occurs for a first time duration, and the contacting of the second abrasive occurs for a second time duration, wherein the second time duration initiates subsequent to the initiation of the first time duration.

16. The method according to claim 12, wherein the disintegrating comprises at least one of disrupting the film via exposure to saliva or mechanical force.

* * * * *